(12) United States Patent
Travers et al.

(10) Patent No.: US 11,166,892 B2
(45) Date of Patent: Nov. 9, 2021

(54) NON-IONIC SURFACTANTS FOR REDUCING FATTY TISSUE

(71) Applicant: CHEMISCHE FABRIK KREUSSLER & CO. GMBH [DE/DE], Wiesbaden (DE)

(72) Inventors: Stephan Travers, Wiesbaden (DE); Petra Gliem, Taunusstein (DE); Matthias Lotter, Wiesbaden (DE); Joachim Otto, Geisenheim-Stephanshausen (DE)

(73) Assignee: CHEMISCHE FABRIK KREUSSLER & CO. GMBH [DE/DE], Wiesbaden (DE)

( * ) Notice: Subject to any disclaimer, the term of this patent is extended or adjusted under 35 U.S.C. 154(b) by 181 days.

(21) Appl. No.: 16/306,142

(22) PCT Filed: May 30, 2017

(86) PCT No.: PCT/EP2017/062956
§ 371 (c)(1),
(2) Date: Nov. 30, 2018

(87) PCT Pub. No.: WO2017/207520
PCT Pub. Date: Dec. 7, 2017

(65) Prior Publication Data
US 2020/0323756 A1    Oct. 15, 2020

(30) Foreign Application Priority Data
May 30, 2016  (EP) .................................... 16171904

(51) Int. Cl.
*A61K 8/39* (2006.01)
*A61K 8/11* (2006.01)
*A61K 9/50* (2006.01)

(52) U.S. Cl.
CPC ................. *A61K 8/39* (2013.01); *A61K 8/11* (2013.01); *A61K 9/5031* (2013.01); *A61K 2800/10* (2013.01); *A61K 2800/91* (2013.01)

(58) Field of Classification Search
None
See application file for complete search history.

(56) References Cited

U.S. PATENT DOCUMENTS

| 5,164,320 | A | 11/1992 | Rutner et al. | |
|---|---|---|---|---|
| 9,687,455 | B2 * | 6/2017 | Dobak | ................ A61K 31/255 |
| 2016/0339042 | A1 * | 11/2016 | Modi | .................... A61K 8/675 |

FOREIGN PATENT DOCUMENTS

| CA | 2872279 A1 | 5/2016 |
|---|---|---|
| WO | 20160138136 A1 | 9/2016 |

OTHER PUBLICATIONS

Dennis Bolten et al., Solubility of Ibuprofen, Phytosterol, Salicylic Acid, and Naproxen in Aqueous Solutions, Chemical Engineering and Technology, vol. 36, No. 3, Mar. 6, 2013, pp. 426-434, www.cet-journal.com.

James Mcdiarmid et al., Results from a Pooled Analysis of Two European, Randomized, Placebo-Controlled, Phase 3 Studies of ATX-101 for the Pharmacologic Reduction of Excess Submental Fat, Aesthetic Plastic Surgery, Springer Verlag, New York, NY, US, vol. 38, No. 5, Jul. 2, 2014, pp. 849-860.

International Search Report for International Application No. PCT/EP2017/062956 dated Jul. 17, 2017.

Jan. 13, 2021 Office Action issued in Japanese Patent Application No. 2018-56530.

* cited by examiner

Primary Examiner — Nannette Holloman
(74) Attorney, Agent, or Firm — Clements Bernard Walker; Christopher L. Bernard

(57) ABSTRACT

The invention relates to a composition for reducing fatty tissue including at least one non-ionic surfactant as an active substance for reducing fatty tissue, wherein said non-ionic surfactant is polidocanol and the solvent is water, and a method for reducing unwanted fatty tissue by administering the composition.

10 Claims, No Drawings

NON-IONIC SURFACTANTS FOR REDUCING FATTY TISSUE

FIELD OF THE INVENTION

The present invention relates to a composition for reducing fatty tissue, to the use of such composition, and to a process for reducing undesired fatty tissue.

BACKGROUND OF THE INVENTION

Increasing obesity in the population is a significant problem, especially in the industrial countries. It has an impact on the expenses of the healthcare systems. At the same time, a beauty ideal that corresponds to a very slim body is propagated as being optimal. In particular, local fat pads, such as in the region of the cheek bones or chin, are already considered unattractive.

Now, various possibilities are known to remove excess fat. For example, an improved method of liposuction is disclosed in EP 1 733 692 A1.

In order to avoid the risks of surgery, injections supposed to remove the corresponding fat pads are increasingly employed. Thus, for example, WO 02/060410 A2 discloses the use of the signaling substance TNF-α (tumor necrosis factor α) in a corresponding injection. The combination of an iron chelating agent, an osmotically effective agent, amino acids and vitamins is disclosed in WO 2013/093947 A1.

It is the object of the present invention to provide a composition for reducing fatty tissue that is sustainable and effective, enriches the prior art, and represents an alternative to the known compositions. In addition, side effects, such as allergic responses or the like, should be as low as possible.

BRIEF SUMMARY OF THE INVENTION

This object is achieved by compositions according to the main claim. Advantageous embodiments are mentioned in the dependent claims. Further, the invention includes the use of the composition, and a process for reducing fatty tissue, as shown in the further independent claims.

DETAILED DESCRIPTION OF THE INVENTION

It has been found that surfactants and, in particular, non-ionic surfactants, are suitable for reducing, and preferably removing, fatty tissues in humans. Such a reduction is obtained by administering an aqueous solution of the surfactants directly into the fatty tissue, so that a composition according to the present invention comprises at least one surfactant, in particular, at least one non-ionic surfactant, as the active substance, and water as the solvent. The water is suitable for corresponding applications, in particular, it is water for injection.

The surfactant is preferably a non-ionic surfactant, especially one selected from polidocanol and/or the Na salt of dihydroxycholanic acid. The non-ionic surfactant polidocanol is particularly preferred. Polidocanol is another name for Lauromacrogol 400, which corresponds to the following formula:

$$C_{12}H_{25}-(O-CH_2-CH_2)_n-OH.$$

Usually, n has an average value of 9. Interchangeable names for polidocanol include, for example, laureth-9, lauromacrogol 400, macrogol lauryl ether (Ph. Eur.), polyethylene glycol lauryl ether, dodecyl alcohol poly-9-glycol ether, hydroxypolyethoxydodecane, or polidocanol 600. Its CAS No. is 9002-92-0, or 3055-99-0.

The following mechanism of action is assumed for the composition according to the invention: The active substance has the effect that liquid from the extracellular matrix (ECM) or lymph can permeate into the fat cell. This results in cell swelling, so that osmotic exchange takes place. Thus, the fat cell releases its content, especially fatty acids, such as triglycerides, and cytoplasm, at least partially, preferably completely. The fatty acids that were stored in the fatty cells until that time can then be excreted from the body. This results in the desired reduction of the fatty tissue.

According to the invention, the polidocanol preferably has an average molecular weight within a range of from 500 to 700, especially from 570 to 600. More preferably, it has a cloud point in water of 80° C. to 90° C.

Both polidocanol and the Na salt of dihydroxycholanic acid are already employed on and in humans for different indications, so that the risk in terms of undesirable effects in the human body is as low as possible. Essentially no negative long-term effects have been known from the previous applications. Surprisingly, a novel use, namely local fat reduction, has now been found, so that the present invention also relates to the use of non-ionic surfactants, especially polidocanol or the Na salt of dihydroxycholanic acid for the local reduction of fatty tissue.

The composition according to the invention may contain a surfactant, especially a non-ionic surfactant, as the active substance. It is also possible that it contains 2, 3 or more different surfactants, especially non-ionic surfactants. Preferably, it contains polidocanol and/or the Na salt of dihydroxycholanic acid. More preferably, the active substance is polidocanol. The content of active substance in the composition is preferably from 0.1% to 15% by weight, especially from 0.3% to 15% by weight, or up to 8% by weight, especially from 0.5% to 5% by weight, or up to 3% by weight, more preferably from 0.8% to 2% by weight, or up to 1% by weight. Too high a surfactant concentration can disrupt the cell membrane of the fatty cells, so that the content of surfactant is preferably 8% by weight or less, especially 5% by weight or less. The content in % by weight is always based on the total weight of the cosmetic composition, which corresponds to 100% by weight.

In addition to the active substance, the aqueous composition may contain further auxiliaries. Auxiliaries are those compounds that may support the effect or improve the stability of the composition. However, an effect of their own with respect to fat removal cannot be attributed to them. However, they may have an effect of their own, such as a reduction of irritation of the tissue that surrounds the fatty tissue to be removed. According to the invention, corresponding auxiliaries are selected, in particular, from anionic, cationic or zwitterionic surfactants, vitamins, amino acids, retardants, solubilizers, and mixtures thereof.

Vitamins and amino acids are added, in particular, to supply the tissue surrounding the fatty tissue with nutrients, so that as low as possible a number of side effects are obtained. In addition, an attractive skin appearance is thus obtained after the treatment.

Solubilizers within the meaning of the present invention are those substances that stably dissolve the non-ionic surfactant in the solvent, i.e., water, so that it can be stably stored over an extended period of time of at least one week or longer, especially two weeks or longer, especially four weeks of longer, preferably three months or longer, especially six months or longer, at room temperature. In addition, a solubilizer provides for a homogeneous distribution of the active substance in the solvent. At the same time, the solubilizer is a substance that does not essentially interact with the fatty tissue, i.e., does not affect the effect of the active substance. At the same time, no further side effects are seen.

Preferably, the solubilizer is presently selected from alcohols, especially monohydric and/or polyhydric alcohols. Polyhydric alcohols within the meaning of the present inventions are preferably dihydric and/or trihydric alcohols. Corresponding dihydric and/or trihydric alcohols with less than 10 carbon atoms, especially with 2 to 5 carbon (C) atoms, are particularly preferred as solubilizers. In addition to the hydroxy groups, the alcohols have no atoms other than carbon and hydrogen. More preferably, the solubilizer is a diol, i.e., a dihydric alcohol with 2 to 5 carbon atoms. These provide for a homogeneous uniform distribution and stabilization of the active substance in the solvent, and at the same time, they do not result in any undesirable side effects. The solubilizer itself is not a solvent. The proportion of solvent is always higher than that of the solubilizer.

A retardant within the meaning of the present invention is a substance that, after the administration of the composition into the fatty tissue, causes the active substance to be constantly released over an extended period of time. This enables a uniform level of action over a desired duration, which enables a particularly efficient fat removal. The retardant may be a microcapsule, for example. For instance, it may be in the form of a core-shell capsule. Such a capsule contains the active substance in the core. The shell consists of a material that is soluble in the fatty tissue, but does not dissolve in the aqueous solution itself. Thus, a retarded release of the active substance only on the site where it is supposed to act may be obtained. At the same time, a transport to the desired site is ensured without enabling a large-area distribution of the active substance in the tissue and thus a reduced concentration at the desired site of action. Microcapsules may also be speckles. Speckles are particles in which there is a matrix. The active substance is then incorporated in this matrix. Both the matrix of speckles and the shell of core-shell capsules may consist of per se known materials, such as preferably polylactides, polyglycolides, polylactic acids, polyglycolic acids, polyanhydrides, polyorthoesters, polyether esters, polycaprolactones, polyester amides, polycarbonates, polycyanoacrylates, polyurethanes, polyacrylates, and mixtures or copolymers thereof. Retardants may also be alginates. Preferably, the retardant is a microcapsule having alginates and/or poly(lactide-co-glycolide) as the matrix or shell material.

Now, in order to enable constant release of the active substance over an extended period of time, the composition according to the invention may contain the active substance in an immediately dissolved state, for example. Further, it may contain microcapsules that contain the retardant and the active substance. If the composition is injected into the fatty tissue, an immediate effect on the site of injection is ensured on the one hand. Then, the retardant ensures a retarded release over a period of at least three days, preferably five days or longer. The period over which the non-ionic surfactant is released can be adjusted individually by appropriately selecting the retardant.

The present invention further relates to the use of a cosmetic composition as described above for reducing fatty tissue by means of injection lipolysis. Injection lipolysis is the administration of the composition by injection for the treatment of local fat deposits. Local fat deposits may be found throughout the body, and in particular, a double chin, sagging cheeks, fat deposits in the upper arms, armpits, belly, hips, saddlebags, fat deposits on the knees, ankles, buttocks, breast and on the inner sides of the upper thighs are reduced thereby. A use of the composition according to the invention is also possible in cases of pseudogynecomasty or of a so-called bull neck.

In another embodiment, the present invention relates to a process for reducing fatty tissue. It includes the administration of a cosmetic composition as described above into the area to be treated. The area to be treated is the region of a body, especially a human body, in which there is a local fat deposit. This may relate to all regions of the human body. In particular, this includes the chin, cheeks, upper arms, armpits, belly, hips, knee, ankles, buttocks, breast and/or upper thighs. The administration is preferably effected by injection. In particular, the injection is performed into the subcutaneous fat tissue of the area to be treated. Thus, the active substance can take effect immediately. Because of the retardant contained in a preferred embodiment, larger amounts of the composition can be introduced especially in areas in which larger deposits of fatty tissues are found, and act there for extended periods of time.

In order to ensure the effect, it is recommendable to repeat the administration. However, repetitions should be done at some interval for the body to have sufficient time to excrete the released fatty acids from the body. Further, the tissue surrounding the treated area should have an opportunity to recover.

Even though the active substances, solvents and auxiliaries are subjected to extended testing, undesirable responses in the body may nevertheless arise. In order that these are kept as low as possible, a time interval of at least one week is to be observed. In particular, the administration is effected at an interval of from 7 to 10 days.

If the composition contains a particularly effective retardant that enables release over a period of 3 days or more, especially of up to 7 days, then the administration is effected at intervals of 18 to 30 days, or even at longer intervals.

The invention claimed is:

1. A composition for reducing fatty tissue, comprising
   a) at least one non-ionic surfactant as an active substance for reducing fatty tissue at a desired site of the fatty tissue, wherein said non-ionic surfactant is polidocanol and content of the non-ionic surfactant is from 0.1% to 15% by weight, and
   b) a solvent, wherein the solvent is water; the composition further comprising a retardant, wherein the retardant is in the form of speckles and the speckles have a matrix, and the retardant is configured to ensure a uniform, retarded release of the polidocanol over a period of time at the desired site.

2. The composition according to claim 1, characterized in that said polidocanol has an average molecular weight within a range of from 500 to 700, and/or a cloud point in water of 80° C. to 90° C.

3. The composition according to claim 1, further comprising one or more auxiliaries selected from vitamins, amino acids, solubilizers, and mixtures thereof.

4. The composition according to claim 3, characterized in that said solubilizer is selected from monohydric alcohols and/or polyhydric alcohols.

5. The composition according to claim 1, characterized in that said matrix comprises polylactides, polyglycolides, polylactic acids, polyglycolic acids, polyanhydrides, polyorthoesters, polyether esters, polycaprolactones, polyester amides, polycarbonates, polycyanoacrylates, polyurethanes, polyacrylates, and mixtures or copolymers thereof.

6. The composition according to claim 1, characterized in that said microcapsule comprises alginates and/or poly(lactide-co-glycolide) as the speckle matrix or shell material.

7. A process for reducing fatty tissue, comprising the administration of a cosmetic composition comprising
   a) at least one non-ionic surfactant as an active substance for reducing fatty tissue at a desired site of the fatty tissue, wherein said non-ionic surfactant is polidocanol, and
   b) a solvent, wherein the solvent is water; the composition further comprising a retardant, wherein the retardant is in the form of speckles and the speckles have a matrix, and the retardant is administered to ensure a uniform, retarded release of the polidocanol over a period of time at the desired site,
   wherein said administration is effected by injection.

8. The process according to claim 7, characterized in that said administration is effected repeatedly.

9. The process according to claim 7, characterized in that said administration is effected repeatedly at intervals of 18 to 30 days.

10. The process according to claim 7, characterized in that said administration is effected repeatedly at intervals of from 7 to 10 days.

\* \* \* \* \*